(12) United States Patent
Yelton et al.

(10) Patent No.: US 7,625,469 B1
(45) Date of Patent: Dec. 1, 2009

(54) NANOELECTRODE ARRAY FOR ELECTROCHEMICAL ANALYSIS

(75) Inventors: William G. Yelton, Sandia Park, NM (US); Michael P. Siegal, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 1004 days.

(21) Appl. No.: 11/081,923

(22) Filed: Mar. 16, 2005

(51) Int. Cl.
*G01N 27/26* (2006.01)
*G01N 27/30* (2006.01)
*G01N 27/403* (2006.01)

(52) U.S. Cl. ............... 204/229.9; 204/194; 204/229.8; 204/280; 205/775; 977/840; 977/888; 977/890; 977/891

(58) Field of Classification Search .............. 204/193, 204/194, 400, 229.8, 229.9, 279, 280; 205/775; 977/700, 840, 888, 890, 891
See application file for complete search history.

(56) References Cited

U.S. PATENT DOCUMENTS

2004/0134778 A1* 7/2004 Stelzle et al. .......... 204/403.01

OTHER PUBLICATIONS

Koehne, J. K., et al. "The fabrication and electrochemical characterization of carbon nanotube nanoelectrode arrays", Journal of Materials Chemistry, vol. 14, No. 4, Feb. 2004, p. 676-684.*
Yelton, W. G., et al. "Nano electrode arrays for in-situ identification and quatification of chemicals in water", Report No. SAND2004-6229, DOE Contract No. AC04-94AL85000, Sandia National Laboratories, Dec. 2004.*
Andrea Cavicchioli, Analysis and Speciation of Traces of Arsenic in Environmental, Food and Industrial Samples by Voltammetry: a Review, Electroanalysis, 2004, 16, No. 9, 697-711.
Y. Bonfil, Characteristics of Subtractive Anodic Stripping Voltammetry of Lead, Cadmium and Thallium at Silver-Gold Alloy Electrodes, Electroanalysis, 2003, 15, No. 17, 1369-1376.
Rosemary Feeney, Voltammetric measurement of arsenic in natural waters, Talanta, 58, 2002, 23-32.
Rosemary Feeney, On-Site Analysis of Arsenic in Groundwater Using a Microfabricated Gold Ultramicroelectrode Array, Anal. Chem., 2000, 72, 2222-2228.
Damien W. M. Arrigan, Nanoelectrodes, nanoelectrode arrays and their applications, Analyst, 2004, 129, 1157-1165.
Cynthia G. Zoski, Ultramicroelectrodes: Design, Fabrication, and Characterization, Electroanalysis, 2002, 14, No. 15-16, 1041-1051.
E. Gileadi, Electrode Kinetics for Chemists, Chemical Engineers, and Materials Scientists, Chapter 27, Wiley-VCH, New York (1993).

* cited by examiner

*Primary Examiner*—Nam X Nguyen
*Assistant Examiner*—J. Christopher Ball
(74) *Attorney, Agent, or Firm*—Kevin W. Bieg

(57) ABSTRACT

A nanoelectrode array comprises a plurality of nanoelectrodes wherein the geometric dimensions of the electrode controls the electrochemical response, and the current density is independent of time. By combining a massive array of nanoelectrodes in parallel, the current signal can be amplified while still retaining the beneficial geometric advantages of nanoelectrodes. Such nanoelectrode arrays can be used in a sensor system for rapid, non-contaminating field analysis. For example, an array of suitably functionalized nanoelectrodes can be incorporated into a small, integrated sensor system that can identify many species rapidly and simultaneously under field conditions in high-resistivity water, without the need for chemical addition to increase conductivity.

18 Claims, 6 Drawing Sheets planar macroelectrode hemispherical nanoelectrode

10um_array_on_au_2 5KV 04111

1_4um_array_4 5KV 04111

NANOELECTRODE ARRAY FOR ELECTROCHEMICAL ANALYSIS

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to electrochemical analysis and, more particularly, to a nanoelectrode array that can be used for in-situ analysis of chemicals in water.

BACKGROUND OF THE INVENTION

Electrochemical analysis is a highly sensitive, chemically selective method for identifying and quantifying many different chemicals in water. Sub-part-per-billion sensitivity levels are achievable for many EPA-regulated chemicals and for many of the chemicals proposed for future regulation. Unfortunately, electrochemical analysis has historically required that field samples be transported to an analytical laboratory where additional laboratory chemicals must be added to the samples before an electrochemical analysis can be performed with bench-scale equipment. This requires skilled laboratory technicians and causes unacceptable time delays when immediate information about the safety of a particular water source is needed. Furthermore, sample degradation may occur during sample transport to the laboratory, thereby causing further uncertainty in the analytical results. Conventional off-site laboratory analysis is also too costly if comprehensive, continuous monitoring of the health of a water distribution system is desired.

The necessary addition of chemicals for currently available electrodes to work well with many water samples is a key limiting factor preventing on-site, real-time measurements and distributed unmanned operation. Due to their size, the macroscale working electrodes most often used in electroanalysis today require the addition of an electrolyte to the solution to adjust the conductivity, ionic strength, and/or pH of the solution before an accurate electrochemical analysis can be made. Recently, there has been emphasis on scaling down the working electrode to microscale dimensions to achieve geometry related increases in the diffusion-limited current density. Unfortunately, the incorporation of microelectrodes in analytical methods is severely hampered by the small faradaic currents (i.e., small analytical signals) typical for these electrodes. Furthermore, microelectrodes also require supporting electrolytes for proper operation. For example, a 1-μm-diameter working electrode typically requires that a supporting electrolyte solution be added to achieve a minimum resistivity of 80-100 Ω-cm. This necessitates the presence of a trained technician to properly adjust solution concentrations.

Further reduction of the electrode dimension from the microscale to the nanoscale can remove these resistivity limitations, enabling unattended operation or direct measurements by simple immersion in a water source without any electrolyte addition. However, because the faradaic current from an individual nanoelectrode is very small, a massive array of nanoelectrodes is required to obtain an adequate current signal. Furthermore, integrated nanoelectrode arrays and portable control electronics are needed to enable reliable electrochemical measurements to be made in the field. Such integrated nanoelectrode arrays are not readily available using current fabrication techniques. The nanoelectrode array of the present invention overcomes the limitations of current electrode designs and can enable both portable, battery-powered field testing and continuous remote system monitoring.

SUMMARY OF THE INVENTION

The present invention is directed to a nanoelectrode array, comprising an electrically conducting substrate, an insulating layer on the substrate, and a plurality of hollow pores formed through the insulating layer to provide a plurality of working nanoelectrodes, wherein each working nanoelectrode has a critical dimension and the plurality of working electrodes has a uniform inter-electrode spacing between each working nanoelectrode. The nanoelectrode array can further comprise a conducting layer deposited on the top surface of the insulating layer to provide a counter electrode. The critical dimension of the plurality of working nanoelectrodes is preferably less than 1 micron and, more preferably, less than 100 nm. The inter-electrode spacing is preferably greater than ten times the critical dimension. The working nanoelectrodes can be functionalized to provide selectivity for a specific analyte.

The invention is further directed to a method for fabricating a nanoelectrode array, comprising depositing a positive resist layer on an electrically conducting substrate, forming a latent image of a pore pattern in the resist layer by nanoscale lithography, and developing the resist to provide a plurality of hollow pores through the resist layer. The method can further comprise depositing a counter electrode layer on the top surface of the resist to provide a sandwich nanoelectrode array.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIG. 5A shows cyclic voltammograms from the low-density nanoelectrode array. FIG. 5B shows cyclic voltammograms from three working electrodes: the low-density gold nanoelectrode array, the high-density gold nanoelectrode array, and the planar gold electrode.

DETAILED DESCRIPTION OF THE INVENTION

Figure 1:
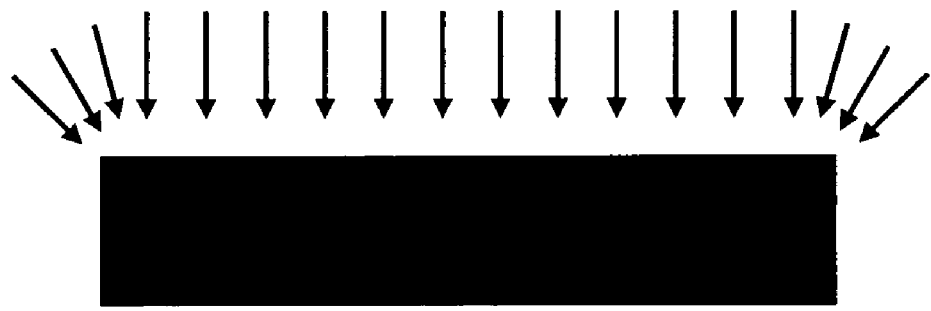
FIG. 1 shows a schematic illustration of macroelectrode with planar diffusion flux with small edge diffusion and nanoelectrode with hemispherical diffusion flux from radial (i.e., three-dimensional) diffusion.
Figure 1:
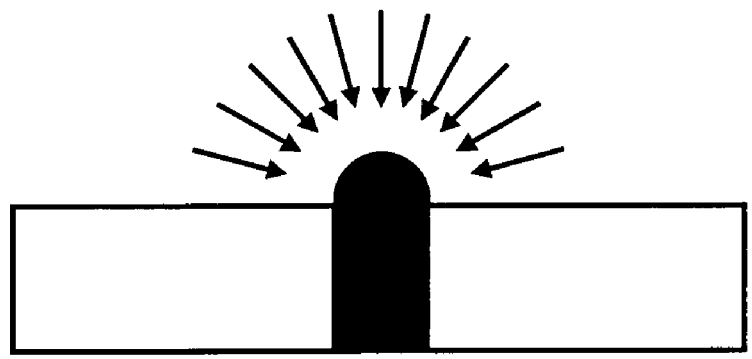

Shown in FIG. 1 is electrochemical diffusion to a planar macroelectrode. In general, the sensitivity of an electrochemical planar electrode is proportional to the diffusion-limited current density $i_d$ after application of a step potential, according to $$i_d = \frac{nFDC}{\delta} \quad (1)$$

such that $\delta = (\pi D t)^{1/2}$ where n represents the number of electrons transferred in the electrochemical reaction, F is Faraday's constant, D is the diffusion coefficient of the electroactive species, C is the bulk concentration of the species in the solution far from the electrode, and $\delta$ is the Nernst diffusion layer thickness that develops away from the electrode when current flows. Thus, the diffusion-limited current density $i_d$ decreases with the square of time t as the Nernst diffusion layer thickness develops and goes to zero for long times (in reality, mass transport by natural convection will become significant at a finite diffusion layer thickness, e.g., 10 μm). Efficient agitation and fast transient measurements have been used to decrease the diffusion layer thickness and thereby increase the rate of diffusion-controlled transport.

Also shown in FIG. 1 is diffusion to a nanoelectrode. As the dimension of the electrode decreases, the edge-effects of current density become dominant as compared to a planar macroelectrode case. The response of a spherical electrode to a potential-step function in the limiting current region is given by $$i_d = nFDC\left(\frac{1}{(\pi Dt)^{1/2}} + \frac{1}{r}\right). \quad (2)$$

Therefore, for a nanoelectrode, the hemispherical diffusion flux of electroactive species becomes nearly independent of time for $(\pi Dt)^{1/2} >> r$ and the diffusion-limited current density at the electrode surface (i.e., ignoring double-layer effects) becomes $$i_d = \frac{nFDC}{r}. \quad (3)$$

This time independence results from the fact that the Nernst diffusion length is increasing (thereby decreasing the diffusion current density) at the same time that the cross section for diffusion is increasing (thereby increasing the diffusion current density). See E. Gileadi, *Electrode Kinetics for Chemists, Chemical Engineers, and Materials Scientists*, Chapter 27, Wiley-VCH, New York (1993).

Therefore, nano-scaled electrodes have geometric advantages over larger electrodes for electrochemical sensing. In particular, nanoelectrodes can extend the range of measurable current densities, due to the fact that limiting current densities are inversely proportional to the radius of the electrode. For example, a nanoelectrode of radius r=40 nm can provide a diffusion-limited current density of about $i_d$=5 A/cm$^2$ for an electroactive species concentration of 10 mM (based on MW=100), with n=2 and D=1×10$^{-5}$. Such limiting current densities cannot be reached at steady state by either rotating disk electrodes operating at 10$^4$ rpm or by any other agitation method. Having a very large limiting current density at steady state, not affected by solution flow, is particularly beneficial in the analysis of trace elements. Furthermore, because of the smaller total currents at nanoelectrodes, electrochemical sensing can be done in highly resistive solutions that would develop large ohmic drops with conventional electrodes.

However, nanoelectrodes do have some disadvantages. Since a single electrode is small, the total faradaic current flowing in the circuit can be very small. For a 40-nm-radius nanoelectrode, the total electrode surface area is only about 5×10$^{-11}$ cm$^2$. Therefore, for a diffusion-limited current density of 1 mA/cm$^2$ the total current is only about 5×10$^{-14}$ A, which can be difficult to measure accurately. Furthermore, these electrodes have a very high volume-to-surface ratio. Therefore, the measurements can be effected by impurities accumulating on the surface during measurement.

A solution to these problems is to use a massive array of nanoelectrodes. By combining a massive array of nanoelectrodes in parallel, the current signal can be amplified while still retaining the beneficial geometric advantages of nanoelectrodes. For example, an array of 40-nm-radius electrodes with an areal density of 1×10$^{11}$ electrodes/cm$^2$ can produce an easily detectable current density of about 5 μA/cm$^2$ (i.e., 5 μA total current from a 1 cm$^2$ array) from a 1-ppb analyte concentration even in solutions with resistivities as high as 10$^6$ Ω-cm, typical of deionized water.

The challenge of designing such an array is obtaining a proper ratio of the electrode radius to the length between electrodes, r/L. If this ratio is too large, the diffusion fields of the individual electrodes will overlap, resulting in a single planar electrode effect. Conversely, if the ratio is too small, the total active surface area of the array is low, making total current flow difficult to measure. Fortunately, the limiting current $i_d$ can be controlled by varying the design and geometry of the array.

When $\delta/r \leq 0.3$, the diffusion layer is small compared to the electrode radius, and the system is in the range of semi-infinite linear diffusion near each large electrode. Therefore, current density is time dependent, and the diffusion-limited current per unit of total surface area $I_d$ is given by $$I_d = i_d\left(\frac{r}{L}\right)^2 = \frac{nFDC}{(\pi Dt)^{1/2}}\left(\frac{r}{L}\right)^2. \quad (4)$$

When $\delta/r \geq 3$ but $\delta/L \leq 0.3$, the diffusion field around each electrode is hemispherical and the overlap between the diffusion fields of neighboring electrodes is negligible. Current (and current density) is then independent of time, according to $$I_d = \frac{nFDC}{r}\left(\frac{r}{L}\right)^2. \quad (5)$$

However, when $\delta/L \geq 3$ (i.e., very long times), there is complete overlap between the diffusion fields of individual electrodes, and the array again appears as one large planar electrode. The current density is again time dependent, according to $$I_d = \frac{nFDC}{(\pi Dt)^{1/2}}. \quad (6)$$

Therefore, each nanoelectrode preferably satisfies $\delta/r \geq 3$, so that the geometric dimensions of the electrode control the electrochemical response and the current density is independent of time. Furthermore, for the individual electrodes to act independently, according to Eq. (5), the diffusion fields should not overlap (i.e., $L/r \geq 10$). If the electrodes are spaced more closely, the resulting diffusion fields from each electrode will overlap each other and the faradaic current collected with an array of nanoelectrodes mimics that observed with a planar electrode. Therefore, the inter-electrode spacing of the nanoelectrodes in the array is preferably ten times greater than the critical dimension of the nanoelectrode so that the current is time independent. Furthermore, to maximize the total current of the array, each nanoelectrode preferably has a critical dimension (i.e., radius for a disc or hemisphere, width for a band) that is in the sub-micron and, more preferably, in the sub-100 nanometer regime.

Such nanoelectrode arrays can be used in a sensor system for rapid, non-contaminating field analysis. For example, an array of suitably functionalized nanoelectrodes can be incorporated into a small, integrated sensor system that can identify many species rapidly and simultaneously under field conditions in high-resistivity water, without the need for chemical addition to increase conductivity. Signal-to-noise ratios can be up to $10^3$-fold greater than conventional planar electrodes. The individual nanoelectrodes within an array can be chemically treated to provide a working electrode surface with enhanced specificity and sensitivity for priority analytes. Further selectivity in the analysis, including discrimination from interfering species in the water, can be derived from the fact that the thermodynamics and kinetics of the heterogeneous electron transfer reaction (i.e., the reduction or oxidation of the analyte) are different from those of many interferents. For example, the deposition of gold surfaces in the nanoelectrode array provides a working electrode surface that is well-suited to the analysis of As(III), As(V), Hg(II), $Hg_xCl_y$ (so-called "reactive mercury"), Cr(III), Cr(VI), Pb(II) and other priority analytes in water sources. Chemical modification of the nanoelectrode surfaces with polymeric coatings can also increase the selectivity and sensitivity of some analyses via preferential adsorption of the analyte in the coating. See, e.g., A. Cavicchioli et al., "Analysis and Speciation of Traces of Arsenic in Environmental, Food, and Industrial Samples by Voltammetry: A Review," *Electroanalysis* 16, 697 (2004); Y. Bonfil et al., "Characteristics of Subtractive Anodic Stripping Voltammetry of Lead, Cadmium and Thallium at the Silver-Gold Alloy Electrodes," *Electroanalysis* 15, 1369 (2003); R. Feeney and S. P. Kounaves, "Voltammetric measurement of arsenic in natural waters," *Talanta* 58, 23 (2002); and R. Feeney and S. P. Kounaves, "On-Site Analysis in Groundwater Using a Microfabricated Gold Ultramicroelectrode Array," *Anal. Chem.* 72, 2222 (2000), which are incorporated herein by reference.

Fabrication of the Nanoelectrode Array

Preferably, the nanoelectrodes are arranged in an orderly array, with a uniform inter-electrode spacing, to achieve the highest total current and an electrochemical response in the three-dimensional (3D) diffusion regime. However, the fabrication of such orderly nanoelectrode arrays has been difficult. Prior nanoelectrode ensembles have had randomly spaced nanoelectrodes and inter-electrode spacings that are either too small, resulting in one-dimensional diffusion from overlap of the diffusion fields of the individual electrodes, or too large, resulting in an inadequate total current. See D. W. Arrigan, "Nanoelectrodes, nanoelectrode arrays and their applications," *Analyst* 129, 1157 (2004); and C. G. Zoski, "Ultramicroelectrodes: Design, Fabrication, and Characterization, *Electroanalysis* 14, 1041 (2002), which are incorporated herein by reference.

The present invention uses nanoscale lithography to pattern an ordered array of nanopores in an insulating template film. The insulating template films can be formed on a conducting substrate. The pores can be modified or filled to from nanoelectrodes. Preferably, the nanoelectrodes are of a uniform cross section (e.g., a circular disc) and are arrayed in an orderly pattern (e.g., a square or hexagonal array). The conducting substrate can be interconnect the nanoelectrodes in parallel. In a parallel array, the measured current of the array can be increased while taking advantage of the improved electrochemical response of each nanoelectrode. Alternatively, the working nanoelectrodes can comprise a plurality of arrays wherein each array is independently addressable through a patterned conductor on the substrate to measure differences in the electrochemical response of each array. The independently addressable arrays can thereby be used to determine different analytes. In FIGS. 3A-3E are shown schematic illustration of methods to fabricate different embodiments of the nanoelectrode array.

The nanopores can be formed in the template film by directed beam or projection methods. For example, electron-beam lithography uses a high energy beam of electrons to form nanopores in a resist-coated substrate by direct writing. An inexpensive positive resist that has a good sensitivity, tone, resolution, and etching resistance, such as poly methyl methacrylate (PMMA), can be used as the template film. Because the electron beam can have a large depth of focus, high-aspect-ration cylindrical pores with uniform diameters can be formed through the resist layer. Most importantly, the pore radius can be sub-100 nm, because the feature resolution achievable with a high energy electron beam is not limited by diffraction, as is the case with optical lithography. The minimum resolution is typically about 10 nm, limited by electron scattering in solids. Furthermore, the registration of the electron beam can be precisely controlled by scanning electrostatic and magnetic fields, enabling the formation of orderly, high-density arrays. Disadvantages are the relatively slow, point-by-point exposure speed and the high cost of current electron-beam lithography systems. Other lithography methods capable of nanoscale resolution, such as extreme ultraviolet, X-ray, or ion-beam lithography can also be used to form the template.

Figure 2A:
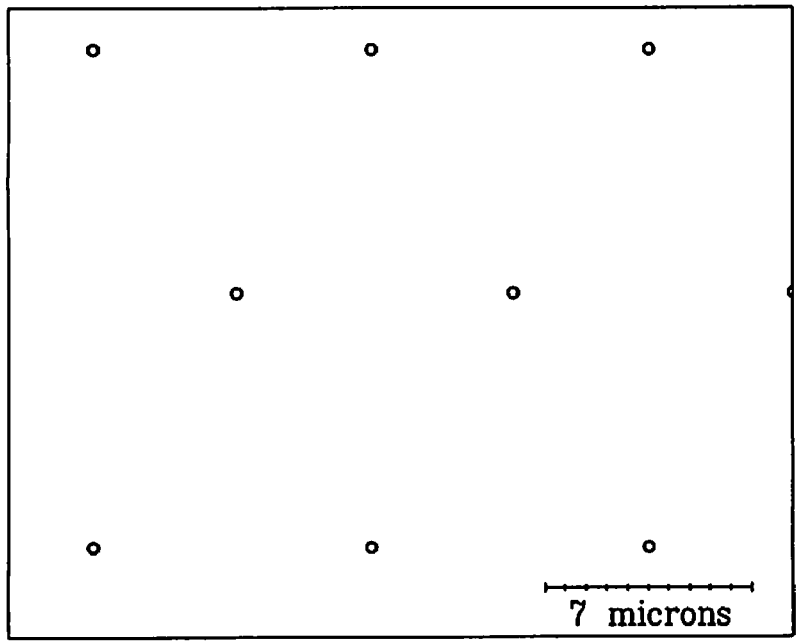
FIGS. 2A and 2B show scanning electron micrographs of resist templates with 200-nm-diameter pores spaced 10 and 1.4 microns apart, respectively, formed by electron beam lithography.
Figure 2B:
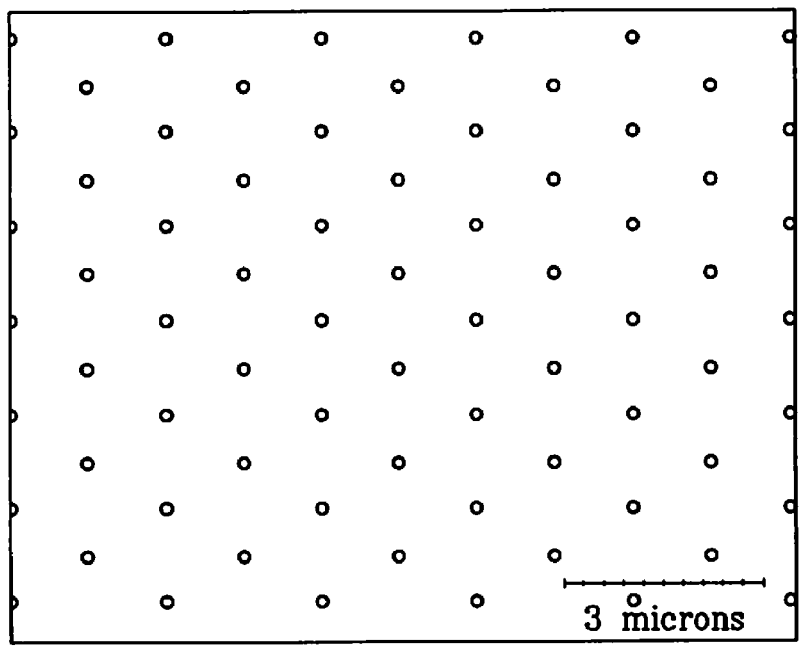

In FIGS. 2A and 2B are shown scanning electron micrographs of resist templates with 200-nm-diameter pores spaced 10 and 1.4 microns apart, respectively, formed by electron beam lithography. A low-density array, having a 10 micron inter-electrode spacing (i.e., L/r=100), provides an electrode density of about 9 million electrodes/cm². A high-density array, having nanoelectrodes spaced 1.4 microns apart (i.e., L/r=14), provides about 90 million electrodes/cm².

Figure 3A:
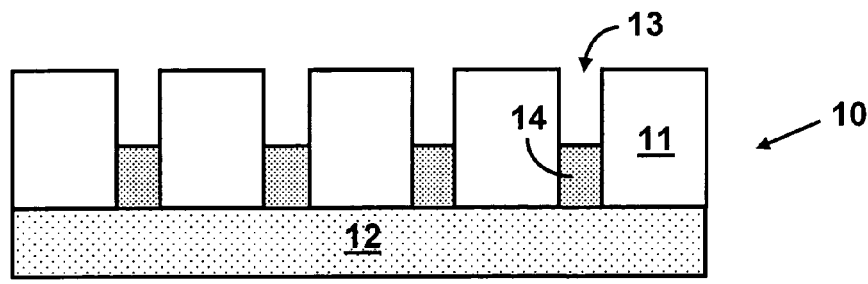
FIGS. 3A-3E show a schematic illustration of methods to fabricate different embodiments of the nanoelectrode array.

In FIG. 3A is shown a schematic illustration of a nanoelectrode array 10 formed in an insulating template film 11 on a conducting substrate 12 to provide a parallel array. For example, the template film can be a layer of PMMA resist that is spun on to a copper substrate coated with an evaporated nickel or gold film. The conducting substrate can alternately comprise a patterned conducting layer on an insulating substrate to provide a plurality of independently addressable arrays. The template film 11 comprises an array of nanoscale hollow pores 13 that can be formed in the template film by nanoscale lithography. The pores can comprise hollow cylinders (to form a disc electrode) or hollow trenches (to form a band electrode). For example, direct writing (either point-by-point or a line) with an electron beam on the resist-coated substrate creates a latent image of the pore pattern in the resist material. The resist can then be developed to remove the exposed resist material and provide a plurality of hollow pores through the resist layer that are substantially perpendicular to the substrate. Preferably, the pores form an orderly array. The pores 13 can be can be left unfilled so that the open pore areas on the conducting substrate 12 provide nanoelectrodes having a recessed disc or band electrode geometry. Alternatively, the pores 13 can be partially filled (as shown) with an electrode material 14, or completely filled to provide an inlaid disc (or band) electrode geometry. The pores 13 can be filled by a number of methods, including electrodeposition, chemical vapor deposition, physical vapor deposition, and sol-gel deposition to form the nanoelectrodes. For example, the pores can be filled using periodic pulse electrodeposition of gold or silver.

Figure 3B:
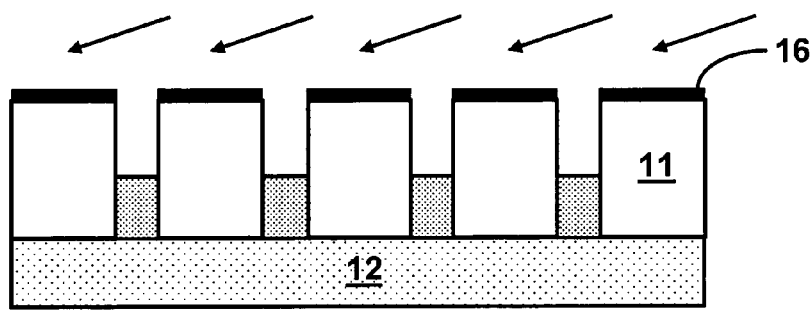
Figure 3C:
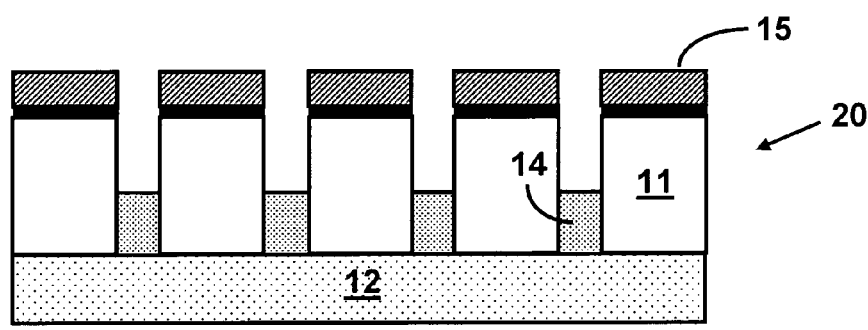
Figure 3D:
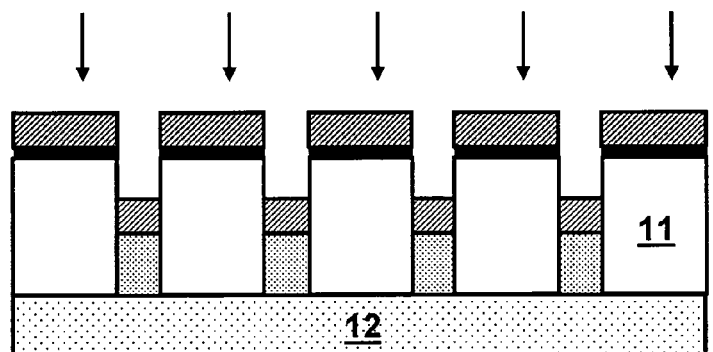
Figure 3E:
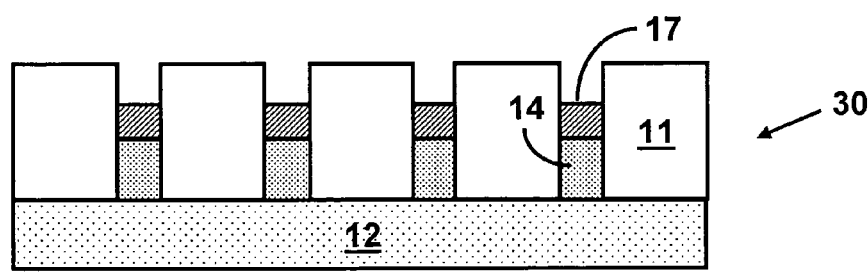

The top surface of the insulating layer can further comprise an integral counter electrode 15 to provide a sandwich nanoelectrode array 20. Since the counter electrode 15 can be very close to the working nanoelectrodes 14, the sandwich array 20 can enable an electrochemical sensor having a very small ohmic drop in solution. Furthermore, the counter electrode 15 can be sized to enhance sensitivity to electrochemical processes that occur at the working nanoelectrodes 14. To fabricate the sandwich nanoelectrode array 20, a thin plating base 16 can be deposited on the bare top surface of the insulating template layer 11 by physical vapor deposition at a low angle, as shown in FIG. 3B. Any residual plating base material that is deposited on the inner surfaces of the pores 13 can be cleared using a pulse of high current. A robust counter electrode 15 can be electroplated on the plating base 16 to provide the sandwich nanoelectrode array 20, as shown in FIG. 3C.

Alternatively, the recessed nanoelectrodes can be further built up in the pores or functionalized by deposition of additional electrode material 17, to provide a functionalized nanoelectrode array 30. A sacrificial material layer 16 can be deposited on the bare top surface of the insulating template layer 11 by physical vapor deposition at a low angle, as shown in FIG. 3B. The additional electrode material 17 can be built up by a line-of-sight deposition that covers the entire exposed area and fills the pores, as shown in FIG. 4D. Finally, the material deposited on the top surface of the template layer can be removed by a lift-off process by dissolving the underlying sacrificial material 16 in a selective etchant, providing the functionalized nanoelectrode array 30 shown in FIG. 4E. Additionally, a counter electrode (not shown) can be deposited on the top surface of template layer by the sandwich nanoelectrode array process described above.

Electrochemical Trace Analysis Using the Nanoelectrode Arrays

Electrochemical processes that occur at the working nanoelectrodes can be measured with a current, voltage, or resistance measuring device to determine the presence of an electroactive analyte. In general, the nanoelectrode array of the present invention can be used to detect any electroactive analyte that exhibits a redox potential. For example, the nanoelectrode array can be used for amperometric, potentiometric, or conductometric sensing.

Chronoamperometry involves stepping the potential of the working electrode from a value at which no faradaic current occurs to a potential at which the surface concentration of the electroactive species is effectively zero. Since mass transport under these conditions is diffusion controlled, the resulting current-time curve reflects the change in concentration gradient in the vicinity of the surface. The current decay therefore indicates the decay of the diffusion layer. For a planar electrode, the current will decay according to Eq. (1). However, for 3D diffusion control of the flux, the decaying current reaches an approximately steady state after a certain time, according to Eq. (2).

Figure 4:
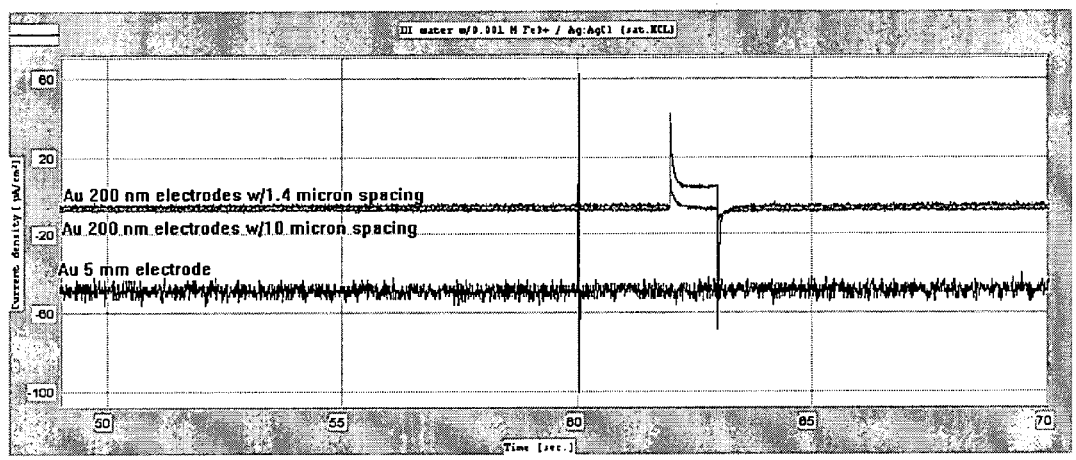
FIG. 4 shows chronoamperometry scans of the current as a function of time after a step potential of +200 mV vs a Ag:AgCl (sat. KCl) reference electrode is applied to low-density array (i.e., 200-nm-diameter gold nanoelectrodes spaced 10 μm apart in a PMMA insulating layer), high-density array (i.e., 200-nm-diameter gold nanoelectrodes with 1.4 μm spacing between electrodes in a PMMA insulating layer), and a 5-mm-diameter planar gold macroelectrode in deionized water with 1.0 mM $Fe^{3+}$.

The current-time profiles shown in FIG. 4 demonstrate the stability of the nanoelectrode arrays compared to the planar electrode in low conductive solutions. Transient background currents are associated with surface redox reactions. Both the low-density and the high-density nanoelectrode arrays have lower signal-to-noise levels at open (or near-open) circuit potentials. After a +400 mV voltage step was applied to the arrays, the current stabilized to a steady state after the charging transit, indicating 3D diffusion control. Conversely, the planar electrode displayed a large transit that quickly decayed into the baseline, indicating semi-infinite linear diffusion.

Cyclic voltammetry (CV) is a widely used electrochemical analysis technique. A voltammogram is a current-potential curve obtained by measuring the current at a working electrode as the potential is linearly ramped in an electrochemical cell containing an electroactive specie. In the presence of these electroactive species, an increase in the current is seen when the potential on the electrode is sufficiently positive (or negative) to cause oxidation (or reduction) of the species present. The magnitude and position of the resulting electrochemical signal can be used as a diagnostic for the species present.

Figure 5A:
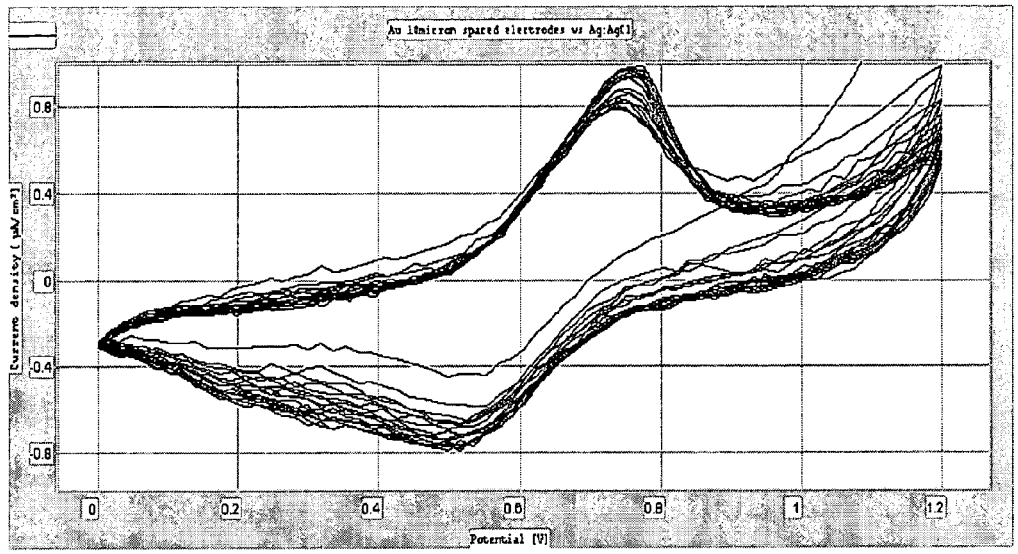
FIGS. 5A and 5B show cyclic voltammograms of the redox peaks for 1.0 mM $Fe^{2+}/Fe^{3+}$ in deionized water vs. a Ag:AgCl reference electrode, using a scan rate of 25 mV/sec.

In FIG. 5A are shown voltammograms from the low-density nanoelectrode array in a dilute solution of 1.0 mM potassium ferricyanide $[K_3Fe(CN)_6]$ in deionized water. Ferricyanide has well known oxidation and reduction peak positions. A standard lab cell, comprising the low-density array as the working electrode, a counter electrode, and an Ag:AgCl reference electrode, at constant temperature without agitation was used to obtain the voltammograms. The voltammograms display a strong oxidation peak at about 750 mV in a solution without the addition of a conducting salt.

Figure 5B:
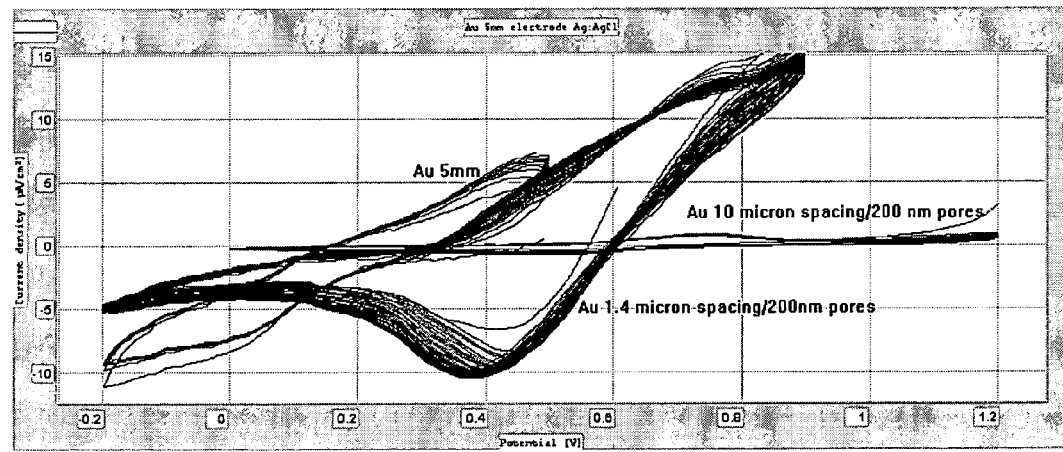

In FIG. 5B are shown voltammograms from three working electrodes in a dilute solution of 1.0 mM potassium ferricyanide $[K_3Fe(CN)_6]$ in deionized water. The working electrodes included the low-density gold nanoelectrode array, the high-density gold nanoelectrode array, and a standard 5 mm planar gold electrode. Because of the scale of the response, the voltammograms obtained with the low-density array are collapsed in the figure. However, as the number of electrodes in the array increase, the response signal increases. Therefore, the CV scan of the high-density nanoelectrode array is much larger than the low-density array.

Electrochemical methods can be used to analyze chemicals in water. Cyclic voltammograms were obtained for the trace element lead using both the planar gold electrode and the low-density gold nanoelectrode array as working electrodes and a quasi-ref/counter electrode. The solution consisted of 0.5 mM $Pb^{2+}$ in a supporting electrolyte of 10 mM KCl and 10 mM $HNO_3$. The CV voltage was scanned from 0 mV to −1000 mV at a scan rate was 25 mV per second.

Figure 6A:
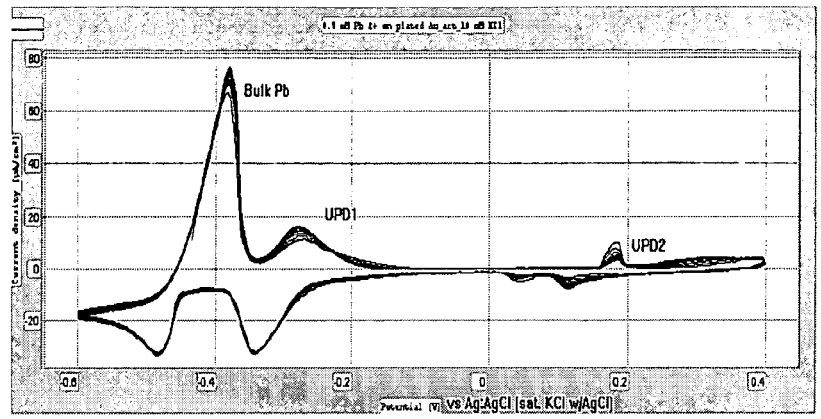
FIGS. 6A-6C show cyclic voltammograms of 0.5 mM $Pb^{2+}$ using the planar gold electrode, the low-density gold nanoelectrode array, and a sandwich nanoelectrode array.

In FIG. 6A is shown a CV scan of 0.5 mM $Pb^{2+}$ using the 5-mm-diameter planar gold electrode, taken at a scan rate of 25 mV/sec. A bulk deposition peak is observed at about −375 mV (vs. a Ag:AgCl reference electrode). The height of the bulk peak, which is proportional to the lead concentration, is about 75 $\mu A/cm^2$. Under potential deposition (UPD) is possible for dissimilar metals at potentials below the standard thermodynamic potential. Therefore, a UPD peak is seen at about −268 mV, resulting from the deposition of a lead monolayer on the gold electrode. The height of the UPD peak is about 17 $\mu A/cm^2$. UPD can be used for trace metal detection at potential windows lower than the standard potential, thus avoiding other competing reactions that are common at higher potentials.

Figure 6B:
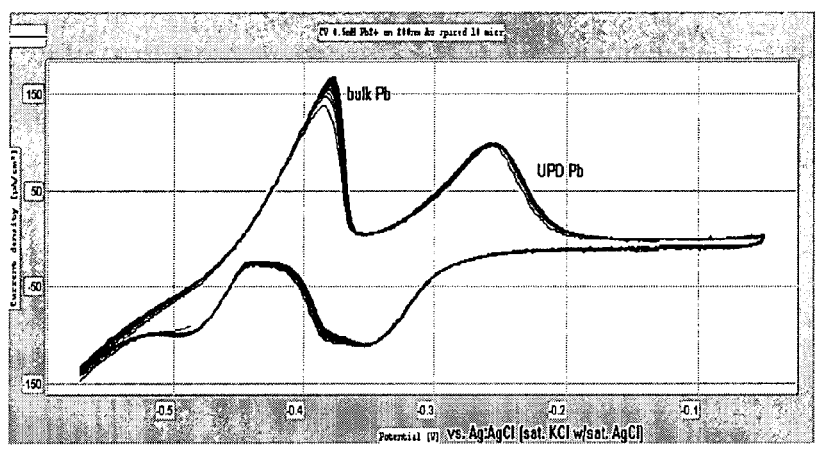

In FIG. 6B is shown a CV scan of $Pb^{2+}$ using the low-density gold nanoelectrode array, having the same footprint as the planar electrode. The scan for the array is similar to that of the planar electrode, although the current density is higher. The height of the bulk peak is about 170 $\mu A/cm^2$, more than twice that of the planar electrode, but with less than 0.3% of the exposed working electrode area. The UPD is almost 6 times greater than the UPD peak generated using the planar electrode under similar test conditions.

Figure 6C:
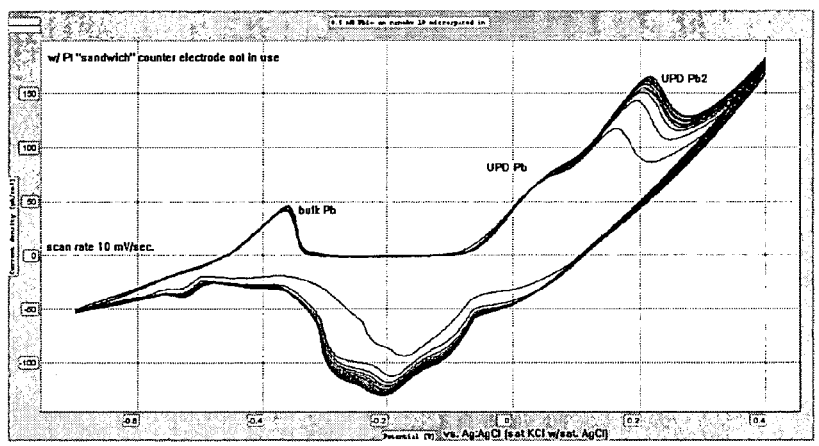

In FIG. 6C is shown a CV scan of $Pb^{2+}$ using the sandwich nanoelectrode array, taken at a scan rate of 10 mV/sec. Again, large bulk and UPD peaks are observed.

The present invention has been described as a nanoelectrode array for electrochemical analysis. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A nanoelectrode array, comprising:
   an electrically conducting substrate,
   an insulating layer on the electrically conducting substrate, thereby providing a top surface opposite the electrically conducting substrate,
   a plurality of hollow pores formed through the insulating layer to provide a plurality of working nanoelectrodes, wherein each working nanoelectrode has a critical dimension and the plurality of working nanoelectrodes has a uniform inter-electrode spacing between each nanoelectrode and wherein the working nanoelectrodes are recessed from the top surface of the insulating layer, and
   a conducting layer deposited on the top surface of the insulating layer to provide a counter electrode.

2. The nanoelectrode array of claim 1, wherein the critical dimension is less than 1 micron.

3. The nanoelectrode array of claim 2, wherein the critical dimension is less than 100 nm.

4. The nanoelectrode array of claim 1, wherein the inter-electrode spacing is greater than 10 times the critical dimension.

5. The nanoelectrode array of claim 1, wherein the inter-electrode spacing is less than 100 times the critical dimension.

6. The nanoelectrode array of claim 1, wherein the plurality of working electrodes comprises a disc electrode.

7. The nanoelectrode array of claim 1, wherein the plurality of working electrodes comprises a band electrode.

8. The nanoelectrode array of claim 1, wherein the plurality of working electrodes forms an orderly pattern.

9. The nanoelectrode array of claim 1, wherein the insulating layer comprises a resist polymer.

10. The nanoelectrode array of claim 1, wherein the working nanoelectrodes are functionalized to provide selectivity for an analyte.

11. The nanoelectrode array of claim 1, wherein the plurality of working nanoelectrodes are combined in a parallel array.

12. The nanoelectrode array of claim 1, further comprising at least one additional independently addressable array.

13. A method for fabricating a nanoelectrode array, comprising:
    depositing a positive resist layer on an electrically conducting substrate,
    forming a latent image of a pore pattern in the resist layer by nanoscale lithography, and
    developing the resist to provide a plurality of hollow pores through the resist layer.

14. The method of claim 13, further comprising depositing a working electrode material in the plurality of hollow pores.

15. The method of claim 14, wherein the depositing step comprises electroplating.

16. The method of claim 13, further comprising depositing a counter electrode layer on the top surface of the resist.

17. The method of claim 13, wherein the resist layer is spun-on the substrate.

18. The method of claim 13, wherein the forming step comprising direct writing the pore pattern in the resist layer by electron beam lithography.

* * * * *